US012097054B2

United States Patent
Davies et al.

(10) Patent No.: US 12,097,054 B2
(45) Date of Patent: Sep. 24, 2024

(54) IMAGING SYSTEM FOR USE IN A FLUOROSCOPY PROCEDURE

(71) Applicant: CEREBRIA LIMITED, London (GB)

(72) Inventors: Justin Davies, Herts (GB); Jeremy Walker, Herts (GB); Christopher Cook, Herts (GB)

(73) Assignee: CEREBRIA LIMITED, London (GB)

( * ) Notice: Subject to any disclaimer, the term of this patent is extended or adjusted under 35 U.S.C. 154(b) by 194 days.

(21) Appl. No.: 17/262,525

(22) PCT Filed: Jul. 18, 2019

(86) PCT No.: PCT/GB2019/052014
§ 371 (c)(1),
(2) Date: Jan. 22, 2021

(87) PCT Pub. No.: WO2020/021240
PCT Pub. Date: Jan. 30, 2020

(65) Prior Publication Data
US 2021/0272286 A1 Sep. 2, 2021

(30) Foreign Application Priority Data
Jul. 23, 2018 (GB) ................................. 1811954

(51) Int. Cl.
*G06T 7/73* (2017.01)
*A61B 6/00* (2006.01)
(Continued)

(52) U.S. Cl.
CPC .............. *A61B 6/032* (2013.01); *A61B 6/465* (2013.01); *A61B 6/469* (2013.01); *A61B 6/481* (2013.01);
(Continued)

(58) Field of Classification Search
CPC ................... G06T 7/0014; G06T 7/73; G06T 2207/10121; G06T 2207/20081;
(Continued)

(56) References Cited

U.S. PATENT DOCUMENTS

| 10,417,763 B2 * | 9/2019 | Lee ...................... G06T 11/203 |
| 2017/0007194 A1 * | 1/2017 | Bialkowski ............ A61B 6/469 |

(Continued)

FOREIGN PATENT DOCUMENTS

| WO | 2010/041201 A1 | 4/2010 | |
| WO | WO-2017106177 A1 * | 6/2017 | ............. A61B 34/20 |

OTHER PUBLICATIONS

International Search Report and Written Opinion mailed Oct. 11, 2019, issued in corresponding International Application No. PCT/GB2019/052014, filed Jul. 18, 2019, 10 pages.

(Continued)

*Primary Examiner* — Shefali D Goradia
(74) *Attorney, Agent, or Firm* — Christensen O'Connor Johnson Kindness PLLC (57) ABSTRACT

We provide an imaging system for use in a fluoroscopy procedure carried out on a subject, the imaging system being configured to receive images of a portion of the subject from an image acquisition device, the imaging system comprising an interface module for displaying images received from the image acquisition device to a user, and an optimisation module for determining, based on an image received from the image acquisition device, one or more properties of the image, wherein the optimisation module is configured to output a control routine.

19 Claims, 4 Drawing Sheets

(51) Int. Cl.

| | |
|---|---|
| *A61B 6/03* | (2006.01) |
| *A61B 6/46* | (2024.01) |
| *A61B 6/50* | (2024.01) |
| *G06F 18/21* | (2023.01) |
| *G06F 18/22* | (2023.01) |
| *G06F 18/24* | (2023.01) |
| *G06N 3/02* | (2006.01) |
| *G06T 7/00* | (2017.01) |
| *G06V 10/25* | (2022.01) |
| *G06V 10/764* | (2022.01) |
| *G06V 10/82* | (2022.01) |
| *G16H 30/20* | (2018.01) |
| *H04N 23/695* | (2023.01) |
| *H04N 23/80* | (2023.01) |

(52) U.S. Cl.
CPC .............. *A61B 6/487* (2013.01); *A61B 6/504* (2013.01); *A61B 6/545* (2013.01); *G06F 18/21* (2023.01); *G06F 18/22* (2023.01); *G06F 18/24* (2023.01); *G06N 3/02* (2013.01); *G06T 7/0014* (2013.01); *G06T 7/73* (2017.01); *G06V 10/25* (2022.01); *G06V 10/764* (2022.01); *G06V 10/82* (2022.01); *G16H 30/20* (2018.01); *H04N 23/695* (2023.01); *H04N 23/80* (2023.01); *G06T 2207/10121* (2013.01); *G06T 2207/20081* (2013.01); *G06T 2207/20084* (2013.01); *G06T 2207/30101* (2013.01); *G06V 2201/03* (2022.01)

(58) Field of Classification Search
CPC .......... G06T 2207/20084; G06T 2207/30101; G16H 30/20; H04N 5/23299; H04N 5/23229; G06V 10/40; G06V 2201/03; A61B 6/465; A61B 6/469; A61B 6/481; A61B 6/487; A61B 6/504; A61B 6/545; G06K 9/6201; G06K 9/6217; G06K 9/6267; G06N 3/02
See application file for complete search history.

(56) References Cited

U.S. PATENT DOCUMENTS

| | | | |
|---|---|---|---|
| 2017/0143292 A1 | 5/2017 | Yun et al. | |
| 2017/0143312 A1* | 5/2017 | Hedlund | A61B 6/037 |
| 2017/0281114 A1 | 10/2017 | Riddell et al. | |
| 2018/0129896 A1* | 5/2018 | Wu | A61B 6/5211 |

OTHER PUBLICATIONS

Combined Search and Examination Report mailed on Jan. 24, 2019, issued in corresponding GB Application No. 1811954.5, filed Jul. 23, 2018, 7 pages.

Office Action mailed Sep. 5, 2023, in corresponding European application No. 19745226.1 filed Jul. 18, 2019, 6 pages.

* cited by examiner

IMAGING SYSTEM FOR USE IN A FLUOROSCOPY PROCEDURE

DESCRIPTION OF INVENTION

The present invention relates to an imaging system for use in a fluoroscopy procedure, and in particular to an optimisation module for use in such a system for optimising a fluoroscopy procedure.

Fluoroscopy is used to form images of portions of patients (or subjects), to allow medical diagnosis, for example. Fluoroscopy provides a series of X-ray images on a monitor, to allow a clinician to analyse and identify a condition of a subject. Typically, the series of images is provided as a constant stream, effectively resembling a video sequence. This facility is an essential component of coronary catheter laboratory and radiology suites, providing diagnostic imaging for medical purposes and interventional medical treatment procedures. It also provides clinicians with a reliable means of tracking the passage of instruments or dye within a subject's body.

However, fluoroscopy carries risk to both subjects and clinicians, primarily in the form of exposure to ionising radiation. For medical practitioners in particular, the continued exposure to radiation during fluoroscopic scanning carried out over several years is a hazard. Multiple reports of presumed occupational radiation-related morbidity and mortality have been demonstrated.

To minimise exposure to radiation, fluoroscopy is preferably performed with the lowest acceptable exposure to ionising radiation for the shortest time necessary. Therefore there is a balance between obtaining optimal image quality (i.e. a sufficiently high frame rate and image area) and minimising extended or repeated imaging for a subject.

During a fluoroscopic imaging session, a clinician may adjust the settings of the image acquisition unit to raise or lower the frequency of images and to increase or reduce collimation (i.e. narrowing of the imaging field). Essentially, the ability to collimate optimally is based on a 'best guess' of which regions are of interest, based on a degree of the clinician's experience.

The present invention relates to optimising fluoroscopic image acquisition for medical purposes, and aims to overcome or ameliorate one or more problems associated with the prior art.

In optimising the acquisition of images in this way, the system also provides an environmentally friendly reduction in energy consumption, by reducing the number of unnecessary images captured (and thus the energy consumed by the system as a whole).

According to a first aspect of the invention we provide an imaging system for use in a fluoroscopy procedure carried out on a subject, the imaging system being configured to receive images of a portion of the subject from an image acquisition device, the imaging system comprising an interface module for displaying images received from the image acquisition device to a user, and an optimisation module for determining, based on an image received from the image acquisition device, one or more properties of the image, wherein the optimisation module is configured to output a control routine.

The imaging system may comprise a control module operable to control the operation of the image acquisition device.

Outputting a control routine may comprise controlling the image acquisition device.

Outputting a control routine may comprise displaying a proposed control action to a user, the control action being an action controlling the image acquisition device.

Outputting a control routine may comprise displaying a proposed control action to a user, prompting the user for confirmation to perform the proposed control action, and controlling the image acquisition device in response to receipt of confirmation from the user.

The or a determined property of the image may be the presence of a feature within the image that is deemed to be significant.

The control routine may include reducing a frame rate of the image acquisition device where no feature deemed to be significant is determined to be present in the image, or increasing frame rate of the image acquisition device where a feature deemed to be significant is determined to be present in the image.

The or a determined property of the image may be the location and area of a feature deemed to be significant within the image.

The control routine may include reducing the area of image acquisition of the image acquisition device to the location and area of the image deemed to be significant.

The or a determined property of the image may be the presence of overlapping features of significance within the image.

The control routine may include changing the angle or position of the image acquisition device relative to the subject or to a surface on which the subject is located.

The or a determined property of the image may be the opacity of vessels identified within the image.

The control routine may include increasing a dosage of dye provided to the subject where the opacity of the vessels is determined to be inadequate.

The optimisation module may have access to a data store comprising a plurality of data each comprising an image and associated classification information.

The associated classification information may include at least one of: presence or absence of a significant feature, opacity of a vessel, presence of overlap in vessels, degree of overlap between vessels and corrective rotation required, and a location and area of significance within an image.

The optimisation module may provide a classification algorithm that is trained using the data held in the data store.

The optimisation module may provide a classification algorithm that compares an observed image to the data held in the data store during use.

The classification algorithm may comprise an artificial neural network associating input images with output control routines.

According to a second aspect of the invention we provide an imaging installation comprising an imaging system according to the first aspect of the invention and an image acquisition device, for use in a fluoroscopy procedure carried out on a subject.

The image acquisition device may be a fluoroscope for using X-rays to obtain images of a portion of a subject.

According to a third aspect of the invention we provide an optimisation module for an imaging system, the optimisation module being configured to receive an image from an image acquisition device, determine, based on the received image, one or more properties of the image, and output a control routine, wherein the control routine comprises instructions for controlling the image acquisition device or instructions to display a proposed control action to a user via a user interface of the imaging system.

The optimisation module may have access to a data store comprising a plurality of data each comprising an image and associated classification information.

The optimisation module may provide a classification algorithm that is trained using the data held in the data store.

The optimisation module may provide a classification algorithm that compares an observed image to the data held in the data store during use.

The classification algorithm may comprise an artificial neural network associating input images with output control routines.

We now describe features of embodiments of the invention, by way of example only, with reference to the accompanying drawings of which

Figure 1:
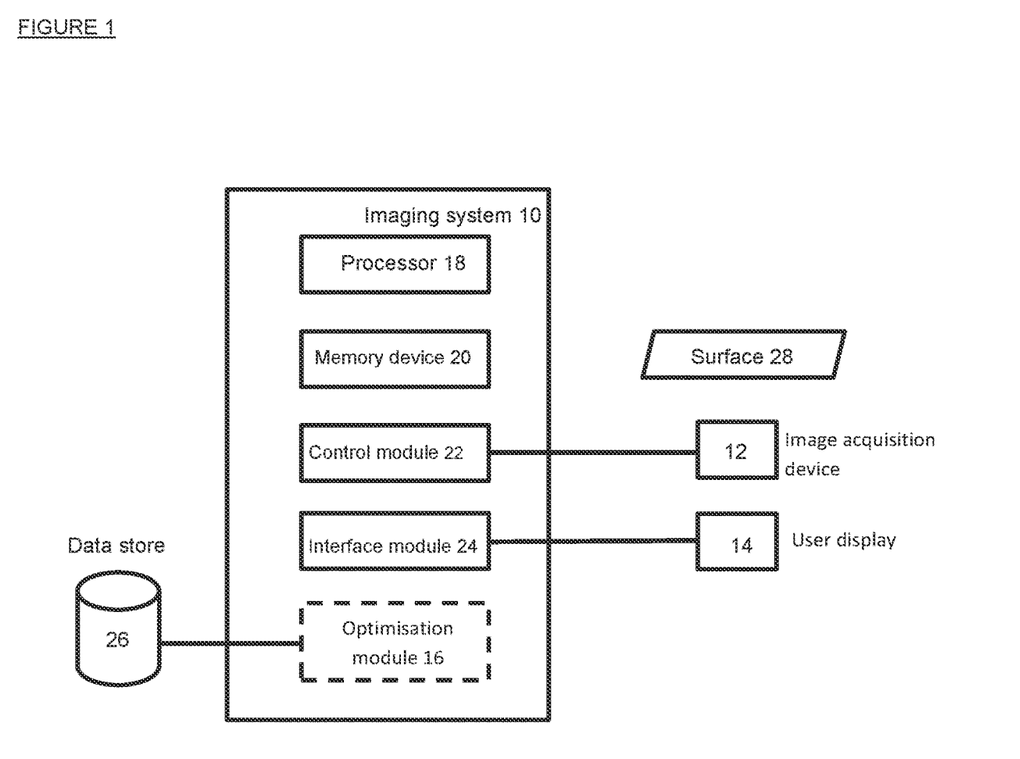
FIG. 1 is a diagrammatic view of an imaging installation including an imaging system according to embodiments of the invention.

With reference to the drawings, we provide an imaging system 10 for performing fluoroscopy. The imaging system 10 interacts with an image acquisition device 12 in that it receives images from the device. The imaging system 10 provides an interface module 24 that includes a user display 14, to allow a clinician to view the output of the image acquisition device 12. The interface module 24 provides information to a clinician.

In embodiments, the interface module 24 also allows the clinician to interact with the imaging system 10 by inputting commands or instructions to control the image acquisition device 12 and/or other aspects of the system 10, for example.

Typically, the system 10 provides a processor 18 and a memory device 20.

The interface module 24 may be provided alongside a control module 22, or the two modules may be formed integrally, such that the control module 22 operates the image acquisition device 12 based either on the instructions or commands of the clinician (provided via the interface module 24) or commands and operating instructions generated by the imaging system 10 in an automated manner, or by a combination of input commands and automated control.

The user display 14 may include one or more screens. In embodiments of the invention, one or more of the screens may also provide elements of a control interface via a touchscreen, for example, those interface elements forming a part of the interface module 24 that is capable of receiving input commands from the user.

It should be understood that the term image acquisition device 12 encompasses the use of at least one device—in particular, the image acquisition device 12 is a fluoroscope for using X-rays to obtain images of a portion of a subject. The device(s) may include a receiver (such as a fluorescent screen) and a source of X-rays. The device(s) may further include one or more cameras and/or X-ray image intensifiers, to improve the visibility of the images produced by the device. In general, the term image acquisition device 12 is meant to encompass one or more devices suitable for outputting images produced by X-ray of the subject, to the imaging system 10.

The control module 22 provides functionality to control the operation of the image acquisition device 12. For example, the control module 22 may turn on or off the X-ray source and/or camera(s) and/or any other components of the image acquisition device 12. The control module 12 controls the capture of images including the rate of capture (also referred to as the frame rate) and the size of the area captured which is directly determined by the application of the X-rays and the collimation of those rays. The term collimation refers to the narrowing of the imaging field to align the rays in a narrower field or otherwise to cause the spatial cross-section of the beam to narrow, and encompasses the techniques well known in the art.

In embodiments, the control module 22 controls the position of the X-ray source (and/or receiver) which is provided on a device moveable relative to the position of the subject, to change the position and/or angle of the source relative to the subject. During user of the system, the subject is located in a lying position, stationary, on a surface 28 fixed in position relative to the imaging system (such as a table or bed). Therefore, the movement of the device is also relative to the fixed surface 28 on which the subject is lying.

The device on which the X-ray source and receiver are positioned may be a C-arm, of the type known in the art. A C-arm provides a C-shaped arm that connects the X-ray source at one end and its detector/receiver at its other end, so that the two may be moved and repositioned relative to the subject (and fixed surface on which the subject lies, in use) to obtain the required images, while ensuring that the source and detector remain aligned with one another.

The images are provided to the clinician (i.e. the 'user') in real-time via the user display 14 and/or may be stored or processed by the imaging system 10.

The imaging system 10 includes an optimisation module 16, to optimise control of the image acquisition device 12. In general terms the optimisation module 16 determines, based on an image (or sequence of images) received from the image acquisition device 12, one or more properties of the image(s), and outputs a control routine based on those properties.

In embodiments, the optimisation module 16 has access to a data store 26 containing training data relating to past image acquisition procedures. The training data include historical data comprising images and/or sequences of images (which may include video sequences). The historical data are supplemented by training information such as classifications of images or portions of images, or identified areas of images that are of interest or importance to a clinician. The historical data preferably contain image data from past image acquisition procedures that have been reviewed by a qualified clinician and classified or labelled accordingly. For example the clinician may classify an image or a portion of an image as being significant, if it contains an image of a part of a subject that will be of significance when carrying out a clinical assessment or procedure. For example, a portion of an image is significant if it shows signs of disease or ailment.

In this way, the training data may provide a list of positive examples of images, features, or portions of images that are significant to a clinician overseeing an image acquisition procedure. Significant portions of an image may include vessels, portions of organs, signs of disease or ailment, or other portions of a body that are generally of interest to a clinician when examining for a particular condition, for example.

In embodiments, the training data may further include negative examples—images, features or portions of images that contain data that are not significant to a clinician. Such portions may include no signs of disease or ailment, or portions of a body that are generally of less interest to the clinician when examining for a particular condition. A clinician may indicate a feature within an image, or a portion of an image containing such a feature, or an entire image, that would not provide useful information to the clinician carrying out the procedure. Such data may be classified as being insignificant. In such embodiments, the training data provide a record of which images, features, or portions of images are significant to a clinician, and those which are not.

In embodiments, the optimisation module 16 is trained using training data from the data store 26, and then when in use, the optimisation module 16 may require no direct access to the data store 26 (where determinations are made using a trained mechanism such as an artificial neural network or other form of trained classifier using a support vector machine, for example). In other embodiments, the optimisation module 16 accesses the training data during use, to make determinations through comparison of the images to data in the training data set (using a high-dimensional clustering or kernel-based classifier, for example).

In some embodiments, the optimisation module 16 has access to the data store 26 to store images processed by the optimisation module 16 in use. The stored images may be supplemented by data recorded from the control module 22 indicating manual control inputs from the clinician made in response to the images, so as to augment the existing training data. In effect, the data recorded from the control module 22 may be used to classify the images, or portions of the images, as being significant or insignificant, based on the actions taken by the clinician.

In use, the optimisation module 16 processes data obtained via the image acquisition device 12 to determine whether they contain significant images/features or not. The optimisation module 16 may receive images directly from the image acquisition device 12, or may receive images that are sent to the user display 14. The images may be received from a screen capture device, for example, which interacts with the user display 14.

In embodiments, if the processed image (or a portion of the image) is determined to be significant, the optimisation module 16 determines that the acquisition framerate should be high, so that the number of images captured is sufficient, and the associated detail contained in those numerous images is of sufficient quality. In embodiments, if the processed image is not determined to be significant, the optimisation module 16 determines that the acquisition framerate should be low. Alternatively, the optimisation module 16 may determine that the framerate should be set to some intermediate value (i.e. between the high and low values) if it is unclear whether the image(s) contain features of significance, or if only a small portion of the image is on significance, for example. These mechanisms limit the exposure of the clinician and subject to potentially harmful X-rays where the images captured are not important to the clinician. It is also important to note that automated systems for performing diagnosis or treatment, or systems assisting clinicians in diagnosis or treatment, rely on receiving an appropriate qualify of image (generally a high-quality image) in order to provide accurate analysis and computer-aided decision-making.

In embodiments, if a portion of a processed image is deemed to be significant, but other portions of the same image are deemed not to be significant, the optimisation module 16 determines that the size of the area of acquisition of the image should be decreased (i.e. increasing collimation). In this way, the image may be focused on only the portion of the image that is significant (or a portion containing a significant feature). In reducing the area of image capture, the area of exposure of the subject to potentially harmful X-rays is reduced.

In embodiments, the optimisation module 16 determines from the processed image or from a sequence of processed images that the image acquisition device should be moved to a different location or to a different angle, relative to the fixed surface 28 on which the subject is lying. The optimisation module 16 may determine that only a portion of the processed image is significant, and if that significant portion is located at or towards an edge region of the image, the optimisation module 16 determines that more significant features lie in that direction (i.e. towards the area deemed to be of significance).

Where the optimisation module 16 makes a determination that the framerate should be high, or low, or should be set to some intermediate value, the imaging system 10 may provide this information to a user via the user display 14. The user may then control the imaging system 10 accordingly, via the interface module 24, to cause the control module 22 to vary or maintain the framerate of the image acquisition device 12. In embodiments, the information is provided to the user in the form of a prompt to confirm a proposal to change the framerate, prior to the image system 10 automatically changing the framerate via the control module 22. In other embodiments, the process of causing the control module 22 to vary or maintain the framerate is carried out automatically by the control module 22 when the determination is made by the optimisation module 16, without requiring input from the user. The information regarding the change (or maintenance) of the framerate may still be displayed to the user via the user display 14.

Similarly, where the optimisation module 16 makes a determination that the area of acquisition of the image (i.e. collimation) should be increased, or decreased, the imaging system 10 may provide this information to a user via the user display 14. The same applies where the optimisation module 16 determines that the image acquisition device 12 should be moved to a different location or to a different angle, relative to the fixed surface 28 on which the subject is lying. In either case, the user may then control the imaging system accordingly, via the interface module 24, to cause the control module 22 to operate the image acquisition device 12 accordingly. As before, in embodiments, the information is provided to the user in the form of a prompt to confirm a proposal to control the image acquisition device 12, prior to the image system 10 automatically controlling the image acquisition device 12. In other embodiments, the process of controlling the image acquisition device 12 is carried out automatically by the control module 22 when the determination is made by the optimisation module 16, without requiring input from the user. In this way, the imaging system 10 is controlled in a way that optimises the process, reducing the amount of X-ray exposure for the clinician and the subject where possible, without compromising the capture of significant images for use by the clinician.

Controlling the image acquisition device 12 to provide an increased or decreased area of image acquisition may involve moving collimation plates (i.e. lead plates) relative to the radiation beam so as to extend or narrow the field of the beam.

In embodiments, optimisation module 16 forms an integral component of an imaging system 10. In other embodiments, the optimisation module 16 is provided as a plug-in to an existing system, in which image data from the image acquisition device 12 or user display 14 (or screen capture device associated with the user display) is received as an input, processed by the optimisation module 16, from which an output provides feedback to a user via the interface module 24, and/or control functionality via the control module 22, as described above.

It should be understood that one or more components of the imaging system may be provided remotely from the other components. For example, the data store 26 may be situated remotely. The data store 26 may comprise a cloud-based data store, accessible via the internet. Alternatively, the data store 26 may be a storage device located alongside the other components, within a self-contained unit, or may be located on local area network, or may have a wired connection with one or more other components of the system.

Similarly the interface module 24 may be located remote from other components of the system. The interface module 24 may, for example, be formed with the user display 14, as a touch screen interface for example. Alternatively, the interface module 24 may include an operator control panel or one or more other hardware components providing control functionality to a user. In embodiments, the interface module 24 and control module 22 may combined to form an integral unit.

To illustrate the method of using the imaging system 10 and optimisation module 16 as described above, we examine a process for using the system in relation to a coronary angiogram procedure.

At the start of a coronary angiogram procedure, the user obtains a non-collimated view (i.e. with a wide area of image acquisition). This image is displayed to the user via the user display 14.

The optimisation module 16 is provided with a sequence of images as described above, and analyses the images for features that it has been trained to classify as being significant. As an example of how this works, in the instance of a coronary angiogram, the images are effectively trained against (i.e. compared to) training data containing images in which the arteries are clearly defined (e.g. with adequate contrast). In addition, the optimisation module 16 determines the position of an angiography catheter in relation to the heart border in order to further refine the optimal degree of collimation.

The optimisation module 16 then identifies an optimal position for the catheter to be positioned, relative to the image. The identification may involve a prompt for the user to position or move the catheter relative to its current position. The optimisation module 16 determines a portion of the image that provides an optimal field of view, and indicates that to the user or provides control via the control module 22 to achieve that optimal field of view. The output of the optimisation module 16 may also provide an overlay to improve the visibility of vessels and arteries, and portions such as an ostium, in images displayed to the user, by increasing contrast for example, or by adding an outline to those features where identified. Outlining features in this way provides assistance to a clinician performing intubation on a subject.

The user may then control the image acquisition device 12 to move it to its optimal position to achieve that optimal field of view by driving the motors to move the metallic lead plates that bound the radiation beam exposure to control collimation, so as to alter the image acquisition area. Once the X-ray has been collimated (i.e. the field of view restricted) to the optimal position, the operator then acquires the fluoroscopic image. This image acquisition may be controlled by means of a foot pedal, in line with routine practice.

Figure 2:
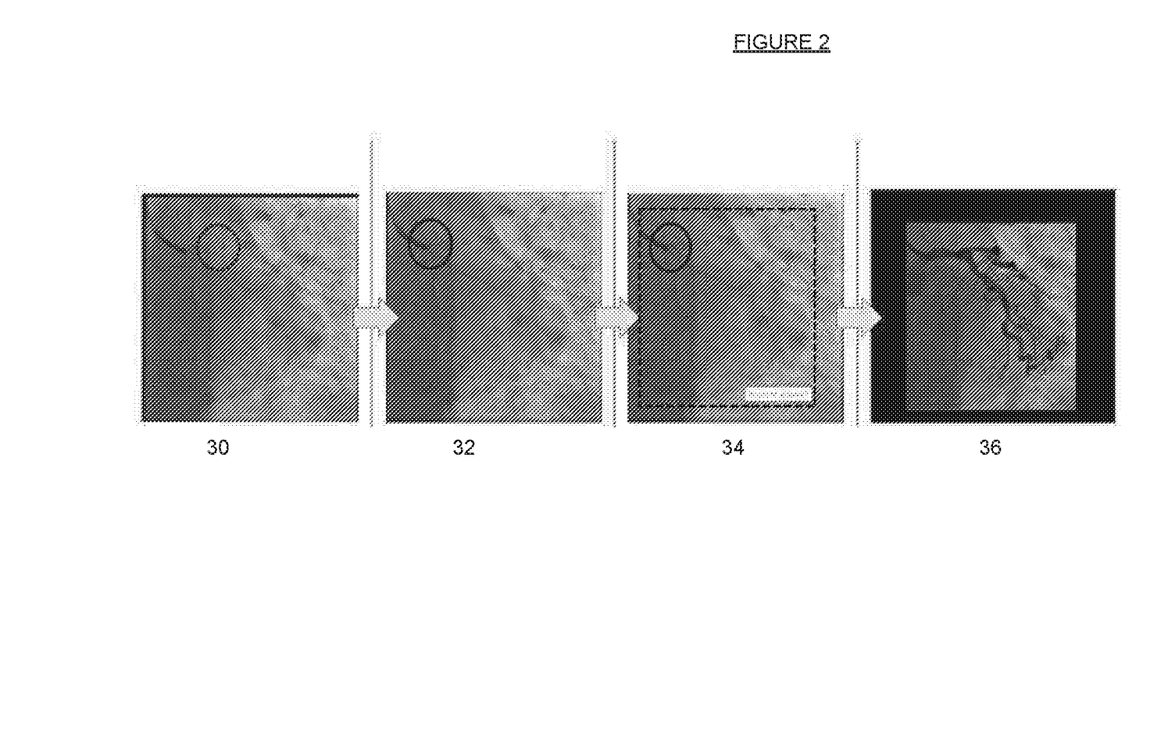
FIGS. 2, 3 and 4 show series of images each illustrating optimised collimation using the system.

With reference to FIG. 2, the optimisation module 16 displays an overlaid circle (30) indicating an optimal position (i.e. to prevent panning). The user then moves the catheter to position it correctly relative to the circle (32). The optimisation module 16 determines a portion of the image that is significant, and a portion of the image that is not significant (34), leading to control of the image acquisition device 12 to a position in which the image is collimated so that the significant portion is captured, and the insignificant portion is not (36).

In embodiments, the optimisation module 16 may provide a control facility to the user directly, via the interface module 24 where that includes an interface via the user display 14. For example, the optimisation module 16 may indicate that the image acquisition area should be reduced, or that the framerate should be reduced, via the interface module 24. The user may then interact directly with the interface module 24 to cause the proposed adjustment to be made.

Figure 3:
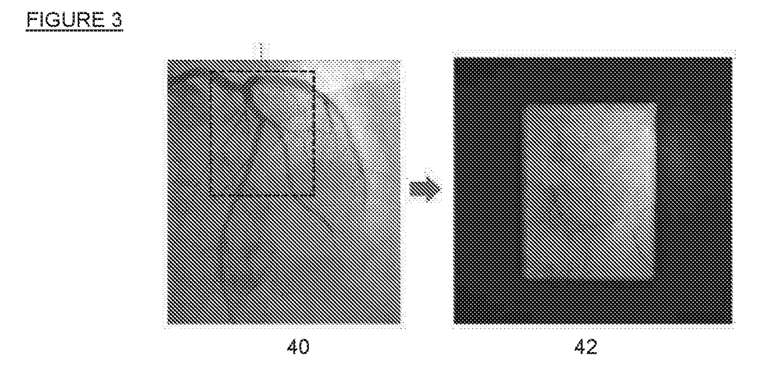
Figure 4:
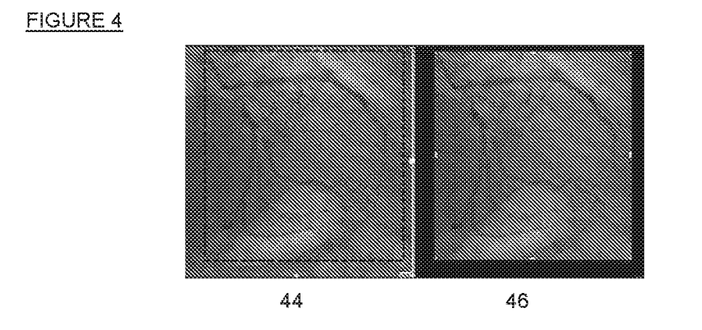

Turning to FIGS. 3 and 4, we note that there are certain steps in the coronary angioplasty procedure where the highest image quality is required. This is so that small adjustments can be made by the clinician to position a stent optimally prior to its deployment. Once deployed, a stent is not retrievable. In these situations, image quality can be improved by collimating out areas from the field of view that are not directly related to the optimal deployment of the stent (e.g. distal vessels (shown as 40,42), as depicted in FIG. 3).

Looking at FIG. 4, the left image 44 shows the original angiogram, with the clinician's label of the region of interest outlined as a superimposed box. The right image 46 shows the segmentation of the angiogram proposed by the optimisation module 16, in which the shaded areas represent areas the algorithm classifies as being outside of the region of interest. The region of interest is indicated by the area in which the original angiogram is viewable. The accuracy of the optimisation module 16, once trained, can be gauged by a comparison of the size and location of the region proposed as being significant against the region indicated by the clinician as being relevant in the training data. It has been shown that, training the optimisation module 16 using the methods described, a high accuracy of prediction is obtained.

The optimisation module 16 is used to detect the stage in the angioplasty procedure where the images must be of highest quality, based on the training data used to train the module. The optimisation module 16 may therefore automatically collimate to optimise image quality.

To provide an example of the training process for the optimisation module, in more detail, we use a deep convolutional encoder-decoder architecture for pixel-wise labelling of images to output a probability matrix describing whether each pixel is inside or outside the recommended image boundary.

The training data may include images alongside data identifying the important (i.e. significant) areas within each image. The identification may be indicated by a rectangular box within the image, identifying the area of significance within the rectangle.

As an example method, a data file is exported for each image, containing data of the image and of its identified region of significance. The image is reshaped to be 224×224 pixels (alternative dimensions may be used in other embodiments, subject to storage and processing restrictions).

A 3 dimensional array of one-hot encoded representations for each channel, where we have two channels, one for 'inside labelled field' (i.e. significant data) and one channel for 'outside labelled field' (insignificant data). One-hot encoding is a binary encoding denoting whether the channel value is significant, for example. For example '1' may identify a significant region, and '0' may identify an insignificant region.

e.g. for a 4×4 image, where only the middle section should appear on the angiogram this would be represented by the following encoding:

[1,1,1,1],[1,0,0,1],[1,0,0,1],[1,1,1,1], [[0,0,0,0],[0,1,1,0], [0,1,1,0],[0,0,0,0]]]

Using this training data, the artificial neural network (ANN) may be encoded as follows. The ANN uses a deep convolutional encoder-decoder architecture. It contains 10 blocks (5 up and 5 down). Each block comprises a series of 3-4 groups containing a Convolution layer, a Batch Normalisation, and a ReLU non-linearity. The "down" groups finish with a MaxPooling layer to cause down-sampling (i.e. taking a max value from each pool of pixels). The "up" groups start with an UpSampling2D layer. The desired training can be achieved when configured such that the Convolutional layers have 64, 128, 256, 512, 512, 512, 512, 512, 256, 128 and 64 filters, respectively, to their blocks. The network then finishes with a Reshape, Permute and a Softmax activation to output a 3D array of one-hot encoded representations in the same format as the training data. It should be understood that ANN of different structures and numbers of layers may be used to train the classification algorithm used by the optimisation module 16.

The ANN is trained using an ADADELTA optimiser (for example) to minimise the Categorical Cross-entropy loss function (as is common in logistic regression). The network may be trained for 20 epochs, using a batch size of images, for example.

In general terms, it should be understood that while a convolutional ANN has been used in this example, other forms of classifier may be employed to identify significant and/or insignificant portions of images for use in the optimisation module 16.

In embodiments, by way of the supervised learning mechanisms employed for training the optimisation module 16, the optimisation procedure effectively tracks the stage of the process being performed by a clinician on a subject. For example, certain imagery or portions of an image are likely to occur at the same stage of the process when performing an angioplasty procedure. The optimisation module 16 therefore is effectively trained to recognise crucial stages of that procedure, and to increase the quality of the images provided to the clinician accordingly (by automatically collimating and/or increasing the frame rate to achieve a suitable image quality).

In embodiments of the invention, in addition to or instead of the optimisation module 16 optimising the frame rate of image acquisition and/or the area or locations of image acquisition, the optimisation module 16 controls the angle of image acquisition relative to the surface 28 fixed in position relative to the imaging system (and therefore relative to the subject). The optimisation module 16 determines from the images obtained by the image acquisition device 12 whether one or more features of importance overlie one another.

Figure 5:
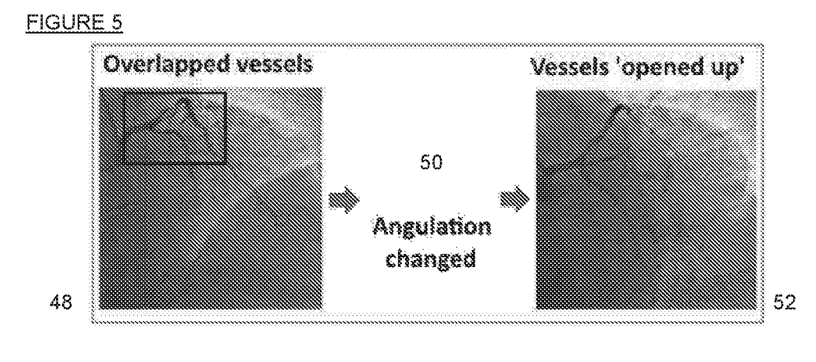
FIG. 5 shows images depicting the results of controlling the angulation of the imaging device.

For example, when viewing a single image (also referred to as a 'projection') of a portion of the coronary system of a subject, one or more vessels may overlap one another. In that case, the clinician may not be able to see one or more of the important feature in sufficient detail. To resolve the issue, the clinician may consider moving the image acquisition device 12 by moving the C-arm, by tilting it, to change its angle relative to the position of the subject (i.e. to the position of the surface 28). In doing so, the angle of acquisition is altered. The user makes minor repeated amendments to the angle of the projection and repeats the X-ray process to try to capture a fluoroscopic image without the vessels overlapping (see FIG. 5, for example). Often this process leads to several images being captured, each exposing the subject and clinician to radiation, and consuming valuable time.

Additionally, if there is no such issue of overlapping vessels of importance to the clinician, the acquisition of multiple images from different angles may not be required as they may provide little or no significant additional information to the clinician.

The optimisation module 16, trained using a training dataset containing images showing overlapping vessels (and/or other overlapping significant features) may provide guidance and/or control functionality to address this problem. For example, in embodiments, the optimisation module 16 is able to detect the presence of overlapping features of significance in an observed image.

In embodiments, the optimisation module 16 determines from the processed image (see 48) or from a sequence of processed images that the image acquisition device 12 should be moved to a different angle relative to the fixed surface 28, to achieve a different projection of the features. Following this determination, the imaging system 10 may provide this information to a user via the user display 14. For example, the system 10 may suggest the next optimal projection (e.g. 'x' degrees X 'y' degrees) that is required to resolve the overlap of the significant features. The user may then control the imaging system 10 accordingly, via the interface module 24, to cause the control module 22 to operate the image acquisition device 12 to achieve the proposed angle and placement (see 50 and 52, in FIG. 5). In embodiments, the information may be provided to the user in the form of a prompt to confirm a proposal to control the image acquisition device 12, prior to the image system automatically controlling the image acquisition device 12. In other embodiments, the process of controlling the image acquisition device 12 is carried out automatically by the control module 22 when the determination is made by the optimisation module 16, without requiring input from the user.

In embodiments, the optimisation module 16 is operable to identify whether a sufficient level of vessel opacification has been achieved before or during an image acquisition process. To perform an angiogram, contrast dye is injected into the coronary vessel during simultaneous fluoroscopic image acquisition. This process increases the opacity of the internal lumen of the vessel and is the primary method for visually identifying narrowed portions of vessels (stenoses). Using such a process, coronary angiography provides the best current test for identifying coronary artery disease.

The process of administering dye manually is reliant on the operator's skill and experience. If too little dye is administered, or the dye is administered too slowly, opacification of the vessel lumen will be suboptimal. This leads to a 'streaming' artefact as the low quantify of dye mixes with the blood in the vessel. For optimal opacification, dye should be sufficient to remove blood from the vessel lumen.

Suboptimal vessel opacification limits the diagnostic yield of the angiogram, leading to uncertainty of the severity of a narrowing in a vessel. Frequently this requires repeat dye injection and image acquisition, causing repeat radiation exposure. In certain situations, repeated suboptimal vessel opacification may render the entire angiogram non-diagnostic, necessitating a repeat of the process.

To address this problem, in embodiments, the optimisation module 16 determines from the images captured by the image acquisition device 12 whether the level of opacification of the vessels shown in the images is adequate. For example, the optimisation module 16, presented with an image, provides a determination of 'adequate' or 'inadequate', subject to classification using a classification algorithm. In embodiments, the classification algorithm applies a threshold to the observed relative level of contrast, or brightness, of portions of the image identified as being vessels compared against the surrounding portions of the image. Values that are lower than a predetermined threshold are determined to be inadequate, for example.

In this way, in embodiments, the optimisation module 16 determines from the processed image or from a sequence of processed images whether a sufficient level of opacity is present in the vessels in the image(s) (and, by association, whether a sufficient level of dye has been injected). Following this determination, the imaging system 10 provides this information to a user via the user display 14. For example, the system 10 may suggest that additional dye should be administered to the subject. The suggestion may include a suggested dosage. The clinician may then apply the dosage manually, and continue the procedure. Or else the clinician may then wait for a prompt from the imaging system 10 confirming that a sufficient level of opacity has been reached.

In embodiments, the user may interact with the imaging system 10 via the interface module 24, to cause the control module 22 to operate a device for administering dye. In this way, the user may confirm a proposed dosage to be administered to the subject. In embodiments, the information may be provided to the user in the form of a prompt to confirm a proposal to control the image acquisition device 12 so as to apply the dosage, prior to the image system 10 automatically controlling device for administering the dosage.

In other embodiments, the process of administering the required dosage may be carried out automatically by the control module 22 when the determination is made by the optimisation module 16, with or without requiring input from the user as desired. Such an automated system is reliant on receiving sufficiently high-quality images from the image acquisition device 12, for which the ability to identify significant features (such as vessels) in the images and to collimate according to those features and at a sufficiently high frame rate, is of course important.

The learning techniques for training a suitable classifier for assessing the level of dye in observed images, or for optimising image acquisition by altering the angle of image acquisition to lessen or remove vessel overlap, may be as previously described—using a training data set provided in the data store 26. As previously described, in embodiments the optimisation module 16 has access to the data store 26 during use, so as to perform comparative assessment with the labelled data in the store. In other embodiments, the optimisation module 16 has no access to the data store 26 during use, and has been trained prior to use of the system so as to provide determinations based on observed images only with no requirement to access past data.

In embodiments, the optimisation module 16 is provided separately from the imaging system 10. In other words, an optimisation module 16 may be retro-fitted to an existing imaging system 10 by communicative connection to the existing system such that the optimisation module 16 is configured to receive an image from an image acquisition device 12, and to determine, based on the received image, one or more properties of the image. The optimisation module 16 then outputs a control routine that includes instructions for controlling the image acquisition device 12, or provides instructions to display to a user via the interface module (i.e. a proposed control action that the user should take to control the image acquisition device 12).

As before, the optimisation module 16 has access to a data store 26 which may be provided integrally with or separate from the optimisation module 16.

Figure 6:
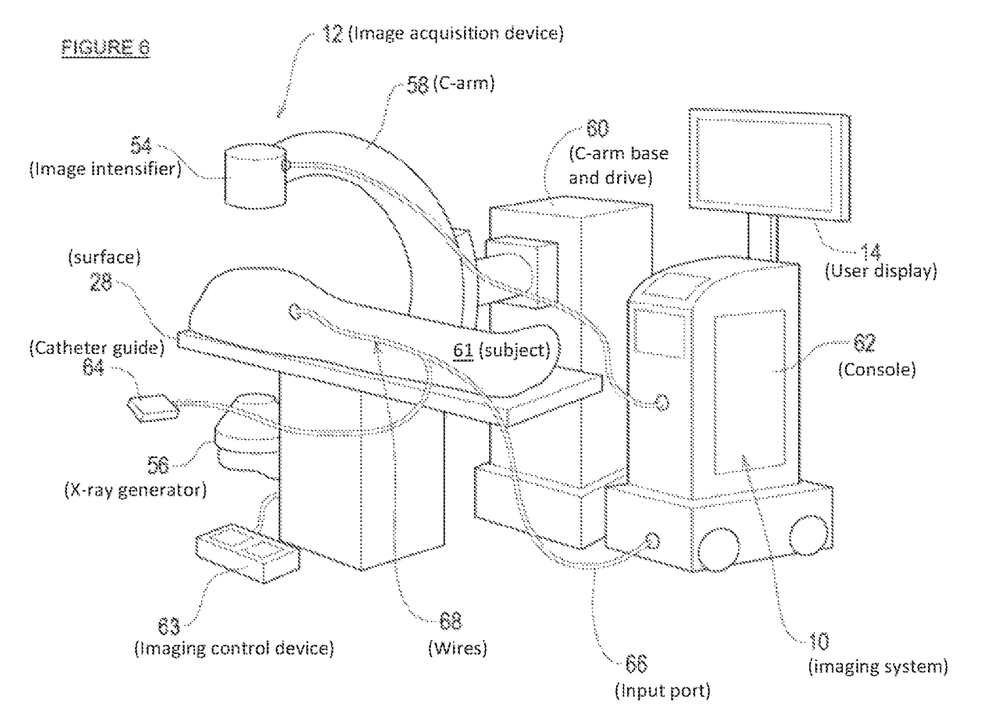
FIG. 6 is an illustration of an imaging installation and associated equipment in situ.

FIG. 6 illustrates the imaging system 10 in the context of an imaging installation in a screening facility, for example. An X-Y platform provides the surface 28 on which the subject 61 is positioned. For conducting aspects of the medical procedure, in examples, a catheter may be used and controlled via a catheter guide 64. The catheter and associated wires 68 may provide data (such as pressure data) that is input to the system via a data input port 66.

The imaging system 10 itself forms part of a console 62 and control system, for controlling aspects of the procedure, the imaging equipment, and the environment. The imaging system 10 is connected to the user display 14. Either the user display 14 or the console 62 or both may provide control functionality via inputs to the control module 22 for controlling the image acquisition device 12. The user display 14, as previously stated, may comprise one or more screens which may be mounted to the console 62 and control system (i.e. providing a standalone unit, as shown), or more commonly may be mounted to a wall of the screening facility, or suspended by mounting equipment from the ceiling or from a wall, for example.

In this example, the image acquisition device 12 comprises an image intensifier 54 (i.e. the receiver/detector) and an X-ray source 56 disposed on either side of a portion of the subject 61, so as to acquire images of the subject 61. The image intensifier 54 and X-ray generator 56 are supported on the C-arm 58, and the components of the image acquisition device 12 are controlled via the C-arm base and drive 60, operating on inputs from an imaging control device 63 such as a foot pedal, as illustrated. Data captured by the image acquisition device 12 is output to the imaging system 10 (i.e. the data comprises the angiogram images).

It is envisaged that the imaging system 10 described herein may be used in combination with automated apparatus for performing diagnostic or treatment routines on subjects, to provide images of features relevant to that procedure, of a sufficient quality, without exposing the subject to unnecessary doses of radiation.

While example embodiments of the invention are described herein, it should be understood that features of different embodiments may be combined with one another, in isolation from one another or in any combination, unless stated otherwise.

When used in this specification and claims, the terms "comprises" and "comprising" and variations thereof mean that the specified features, steps or integers are included. The terms are not to be interpreted to exclude the presence of other features, steps or components.

The features disclosed in the foregoing description, or the following claims, or the accompanying drawings, expressed in their specific forms or in terms of a means for performing the disclosed function, or a method or process for attaining the disclosed result, as appropriate, may, separately, or in any combination of such features, be utilised for realising the invention in diverse forms thereof.

The invention claimed is:

1. An imaging system for use in a fluoroscopy procedure carried out on a subject, the imaging system being configured to receive images of a portion of the subject from an image acquisition device, the imaging system comprising:
an interface module for displaying images received from the image acquisition device to a user, and
an optimisation module for determining, based on an image received from the image acquisition device, one or more properties of the image,
wherein the optimisation module provides an artificial neural network trained on a plurality of data each comprising a training image and associated classification information, the classification information including first indications provided by a clinician of features within the training images classified as significant, and the classification information including second indications provided by a clinician of features within the training images classified as insignificant, wherein the first indications are separate from the second indications, and wherein the first indications and second indications together identify less than an entirety of content of the training images as either significant or insignificant;
wherein the optimisation module is configured to determine the location and area of a feature determined to be significant within the image received from the image acquisition device using the artificial neural network, and
wherein the optimisation module is configured to output a control routine.

2. An imaging system according to claim 1, wherein the imaging system comprises a control module operable to control the operation of the image acquisition device.

3. An imaging system according to claim 2, wherein outputting a control routine comprises controlling the image acquisition device.

4. An imaging system according to claim 2, wherein outputting a control routine comprises displaying a proposed control action to a user, prompting the user for confirmation to perform the proposed control action, and controlling the image acquisition device in response to receipt of confirmation from the user.

5. An imaging system according to claim 1, wherein outputting a control routine comprises displaying a proposed control action to a user, the control action being an action controlling the image acquisition device.

6. An imaging system according to claim 1, wherein the control routine includes reducing a frame rate of the image acquisition device where no feature deemed to be significant is determined to be present in the image, or increasing frame rate of the image acquisition device where a feature deemed to be significant is determined to be present in the image.

7. An imaging system according to claim 1, wherein the control routine includes reducing the area of image acquisition of the image acquisition device to the location and area of the image deemed to be significant.

8. An imaging system according to claim 1, wherein a determined property of the image is the presence of overlapping features of significance within the image.

9. An imaging system according to claim 8 wherein the control routine includes changing the angle or position of the image acquisition device relative to the subject or to a surface on which the subject is located.

10. An imaging system according to claim 1, wherein a determined property of the image is opacity of vessels identified within the image.

11. An imaging system according to claim 10, wherein the control routine includes increasing a dosage of dye provided to the subject where the opacity of the vessels is determined to be inadequate.

12. An imaging system according to claim 1, wherein the artificial neural network associates input images with output control routines.

13. An imaging installation comprising an imaging system according to claim 1 and an image acquisition device, for use in a fluoroscopy procedure carried out on a subject.

14. An imaging installation according to claim 13, wherein the image acquisition device is a fluoroscope for using X-rays to obtain images of a portion of a subject.

15. A data processing device for an imaging system, the data processing device storing an artificial neural network trained on a plurality of data each comprising a training image and associated classification information, the classification information including first indications provided by a clinician of features within the training images classified as significant, and the classification information including second indications provided by a clinician of features within the training images classified as insignificant, wherein the first indications are separate from the second indications, and wherein the first indications and second indications together identify less than an entirety of content of the training images as either significant or insignificant, the data processing device being configured to:
receive an image from an image acquisition device,
determine, based on the received image, a location of a feature determined to be significant within the image using the artificial neural network, and
output a control routine, wherein the control routine comprises instructions for controlling the image acquisition device or instructions to display a proposed control action to a user via a user interface of the imaging system.

16. A data processing device according to claim 15, wherein the artificial neural network associates input images with output control routines.

17. A non-transitory computer-readable medium having computer-executable instructions stored thereon that, in response to execution by one or more processors of a data processing device of an imaging system having an image acquisition device and a user interface, cause the data processing device to:
process an image received from the image acquisition device, by:
determining, based on the received image, a location of a feature determined to be significant within the image using an artificial neural network, the artificial neural network having been trained on a plurality of data each comprising a training image and associated classification information, the classification information including first indications provided by a clinician of features within the training images classified as significant, and the classification information including second indications provided by a clinician of features within the training images classified as insignificant, wherein the first indications are separate from the second indications, and wherein the first indications and second indications together identify less than an entirety of content of the training images as either significant or insignificant, and
output a control routine, wherein the control routine comprises instructions for controlling the image acquisition device or instructions to display a proposed control action via the user interface.

18. An imaging system for use in a fluoroscopy procedure carried out on a subject, the imaging system being configured to receive images of a portion of the subject from an image acquisition device, the imaging system comprising:
- an interface module for displaying images received from the image acquisition device to a user, and
- an optimisation module for determining, based on an image received from the image acquisition device, one or more properties of the image,
- wherein the optimisation module provides an artificial neural network trained on a plurality of data each comprising a training image and associated classification information identifying significant features within the data,
- wherein the optimisation module is configured to determine within the image received from the image acquisition device using the artificial neural network the location of a first feature determined to be significant and a second feature determined to be significant, and to determine that the first feature overlaps the second feature within the image, and
- wherein the optimisation module is configured to output a control routine, the control routine including changing the angle or position of the image acquisition device relative to the subject or to a surface on which the subject is located.

19. A data processing device for an imaging system, the data processing device storing an artificial neural network trained on a plurality of data each comprising a training image and associated classification information identifying significant features within the data, the data processing device being configured to:
- receive an image from an image acquisition device,
- determine within the image received from the image acquisition device using the artificial neural network the location of a first feature determined to be significant and a second feature determined to be significant, and to determine that the first feature overlaps the second feature within the image, and
- output a control routine, wherein the control routine comprises instructions for changing the angle or position of the image acquisition device relative to the subject or to a surface on which the subject is located, or instructions to display a proposed change to the angle or position of the image acquisition device relative to the subject or to a surface on which the subject is located to a user via a user interface of the imaging system.

* * * * *